United States Patent
Oster et al.

(10) Patent No.: US 6,691,821 B2
(45) Date of Patent: Feb. 17, 2004

(54) CUSTOMIZABLE SPILT STEM STETHOSCOPE AND A METHOD FOR PROVIDING SAME

(75) Inventors: Craig D. Oster, Oakdale, MN (US); Douglas W. Voegeli, Stillwater Township, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 35 days.

(21) Appl. No.: 09/948,971

(22) Filed: Sep. 7, 2001

(65) Prior Publication Data

US 2003/0047376 A1 Mar. 13, 2003

(51) Int. Cl.[7] .................................................. A61B 7/02
(52) U.S. Cl. ........................................................ 181/131
(58) Field of Search ................................ 181/131, 132, 181/133, 134, 135, 137

(56) References Cited

U.S. PATENT DOCUMENTS

| | | |
|---|---|---|
| 3,108,652 A | 10/1963 | Littman |
| 3,152,659 A | 10/1964 | Littmann |
| 3,168,160 A | 2/1965 | Littmann et al. |
| 3,168,161 A | 2/1965 | Littmann |
| 3,295,631 A | 1/1967 | Machlup |
| 3,437,172 A | 4/1969 | Allen |
| 3,504,760 A | 4/1970 | LIttman |
| 3,570,625 A | 3/1971 | Allen |
| 3,618,697 A | 11/1971 | Littmann et al. |
| 3,951,230 A | 4/1976 | Littmann |
| 4,200,169 A | 4/1980 | MacDonald et al. |
| 4,440,258 A | 4/1984 | Packard |
| 4,913,259 A | 4/1990 | Packard |
| 5,111,904 A | 5/1992 | Packard et al. |
| 5,324,471 A | 6/1994 | Packard et al. |
| 5,380,182 A | 1/1995 | Packard et al. |
| 5,932,849 A | 8/1999 | Dicken |
| 6,026,170 A | 2/2000 | Dicken et al. |

*Primary Examiner*—Kimberly Lockett
(74) *Attorney, Agent, or Firm*—Daniel R. Pastirik

(57) ABSTRACT

A stethoscope having a binaural and a chestpiece in acoustic communication with that binaural. The chestpiece has at least one microphone in acoustic communication with a hollow stem, with this stem having a slot. The binaural is on the type with a tubing assembly having two lumens, these lumens being separated by a wall. Upon assembly, the tubing assembly engages the stem with the wall disposed within the slot. A method of providing a custom stethoscope is also disclosed.

20 Claims, 3 Drawing Sheets

CUSTOMIZABLE SPILT STEM STETHOSCOPE AND A METHOD FOR PROVIDING SAME

TECHNICAL FIELD

The invention relates generally to stethoscopes and, more particularly to the way stethoscopes are prepared for their intended user.

BACKGROUND

Stethoscopes have long been used by health care professionals to monitor acoustic communication. Typically stethoscopes have been comprised of a microphone or chestpiece, a sound transmission mechanism and an earpiece assembly. The chestpiece is adapted to be placed near or against the skin of a patient for gathering the auscultatory sounds. The sound transmission mechanism transmits the gathered sound to an earpiece, or a pair of earpieces called a binaural, where the physician or other health professional may monitor the sound.

Recently, some stethoscopes have utilized electronics for at least part of the sound processing path. In most of these devices, the auditory sound is picked up by a microphone usually located in a detection device which is similar to the chestpiece of a conventional acoustic stethoscope in external appearance. The electrical signal from the microphone is then processed electronically and is coupled to a speaker, or speakers, where the electrical signal is converted back into an auditory sound for reception by the health care professional. Of course, other electronic analysis or display of the auscultatory sound may be performed by the signal processor, in addition to the usual conversion back into an auditory sound.

Stethoscopes commonly include a tubing assembly having twin, smooth-walled sound pathways extending from the chestpiece to the ear tips. Preferably these pathways are free of sound leakage and each pathway has a constant diameter along its entire length. Often preferred stethoscopes contain a pair of passageways formed in flexible tubing that is molded side-by-side in a one-piece construction for a major portion of the distance between chestpiece and ear tubes. In such constructions, each pathway is conveniently a lumen within a dip-molded polymeric tubing assembly, the two lumens being separated by a wall. Stethoscopes made in this way have enjoyed commercial success as the Littmann™ Cardiology and Master Cardiology stethoscopes, available from 3M Company of St. Paul, Minn.

Typically in such constructions, the final product of the tubing assembly intended for connection to the chest piece is molded in predetermined lengths of tubing assembly. Each length that is to be offered to a customer must be inventoried separately, both by the manufacturer and the distributor. If a wide range of colors or other custom features are to be offered even more must be inventoried. The present art lacks a way of providing the acoustic benefits of a twin lumen construction while at the same time minimizing inventory.

SUMMARY OF THE INVENTION

The present invention solves this problem by providing a specialized chest piece that will adapt to a dual lumen binaural, without that binaural having a molded-in connection. This allows binaurals for stethoscopes to be manufactured in a generic fashion at the maximum desirable length on the expectation that they can be cut down to the length the customer desires at the time of assembly.

More particularly, in one aspect the present invention provides a stethoscope having at least one pair of elongated ear tubes and a chestpiece in acoustic communication with the elongated ear tubes. The chestpiece is in acoustic communication through an adapter comprising a hollow stem, with this stem having a slot therein. A tubing assembly acoustically connects the at least one chestpiece to the ear tubes. The tubing comprises a wall that defines separate twin passages extending throughout the length of the tubing and that is adapted for connecting to the slot of the hollow stem of the chestpiece thereby forming twin air columns extending between the at least one chestpiece and the upper ends of the ear tubes.

Alternatively, the present invention provides a stethoscope having a binaural and a chestpiece in acoustic communication with that binaural. The chestpiece has at least one microphone in acoustic communication with a hollow stem, with this stem having a slot. The binaural is of the type with a tubing assembly having twin, smooth-walled sound pathways extending from the chestpiece to the ear tips. Each pathway contains a lumen within a dip-molded polymeric tubing assembly with the two lumens being separated by a wall. In a preferred embodiment, a stethoscope is provided in which the pair of pathways formed in the flexible tubing are molded side-by-side in a one-piece construction for a major portion of the distance between chestpiece and ear tubes. Preferably these pathways are free of sound leakage and each pathway has a constant diameter along its entire length. Upon assembly, the tubing assembly engages the stem with the wall disposed within the slot. In most preferred embodiments the binaural will have a pair of ear tubes, each ear tube in acoustic communication with one of the lumens.

In another aspect, the present invention comprises a method of providing a custom stethoscope to a customer, comprising the steps of 1) fabricating a chest piece comprising at least one chestpiece in acoustic communication with a hollow stem, the stem having a slot therein; 2) fabricating elongated ear tubes having twin passages separated by a wall; 3) cutting the tubing assembly to a desired tubing assembly length as determined by a customer; and 4) assembling the stethoscope by engaging the tubing assembly with the stem, with the wall disposed within the slot.

The present invention also comprises a method of providing a custom stethoscope to a customer, comprising the steps of 1) fabricating a microphone comprising at least one microphone in acoustic communication with a hollow stem, the stem having a slot therein; 2) fabricating binaurals having twin lumens separated by a wall; 3) cutting the tubing assembly to the desired tubing assembly length as determined by a customer; 4) assembling the custom stethoscope by engaging the tubing assembly with the stem, with the wall disposed within the slot. Additionally, at least one additional feature of the stethoscope can be customized from the group consisting of tubing assembly color, microphone type, and eartip type.

The present invention overcomes many of the drawbacks associated with the prior art methods by enabling the manufacturing of the binaurals in a generic (i.e. uniform) fashion at the maximum desirable length with the expectation that they can be cut down to the length determined by the customer. These and other objects of the present invention will be apparent in view of the following description of the invention and the preferred embodiments.

BRIEF DESCRIPTION OF THE DRAWINGS

In the several figures of the attached drawing, like parts bear like reference numerals, and.

DETAILED DESCRIPTION OF PREFERRED EMBODIMENT

Figure 1:
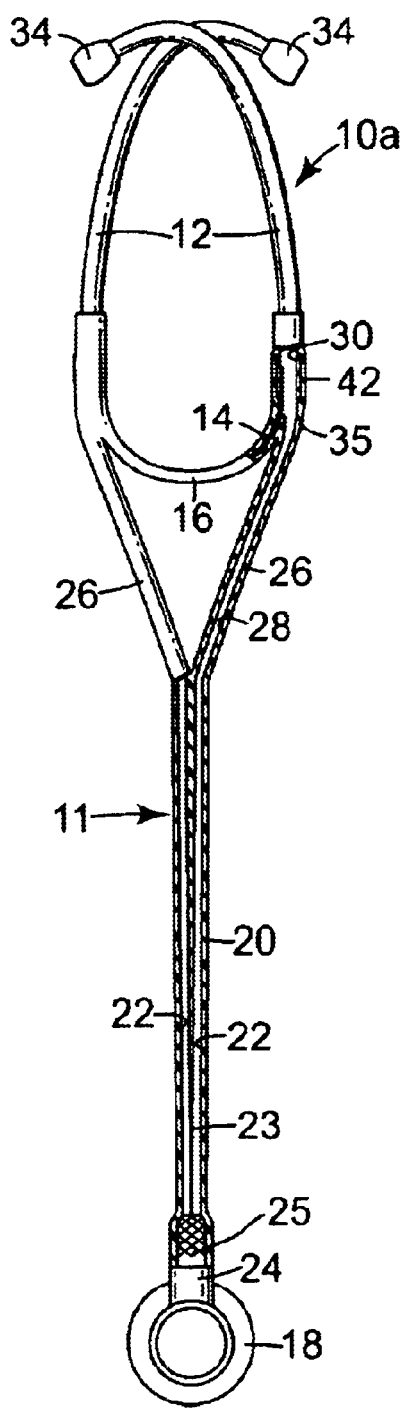
FIG. 1 is a face view of a stethoscope broken away and shown in section.

Referring now to FIG. 1, a face view of a common stethoscope broken away and shown in section is illustrated. The stethoscope 10 includes a binaural 11 having a pair of ear tubes 12 secured together by a prestressed leaf spring 14 optionally enclosed in tubing 16. A conventional chestpiece 18 is attached to ear tubes 12 by elongated flexible tubing 20 which contains dual lumens 22 to serve as sound-conveying air passages and which run side-by-side within a common structure of flexible plastic tubing such as polyvinyl chloride for a major portion of the distance between chestpiece 18 and ear tubes 12. The two lumens 22 are separated by a wall 23. In the lower end of tubing 20 which attaches to chestpiece 18, lumens 22 merge into a single molded in connection 25 adapted to be coupled to a stem 24 of an appropriate chestpiece 18. The stem 24 serves as an adapter to make a connection between the binaural 11 and the rest of the chestpiece 18. The upper end of tubing 20 bifurcates into coupling arms 26, each of which attaches to one of the ear tubes 12. The air passages 22 are continued as air passages 28 in the coupling arms which are in turn continued as air passages 30 in the ear tubes 12.

The binaural ear tubes 12 have upper ends suitably curved toward each other to allow insertion into the ears of the wearer. Ear tips 34 are attached to the upper ends of ear tubes 12 to provide cushioning for the ears and also to insulate the ears against outside sounds. The lower end portions 35 of ear tubes 12 extend into the respective coupling arms 26 of flexible tubing 20, and an air-tight junction is formed between air passages 28 of coupling arms 26 and air passages 30 of the respective ear tubes to which they are joined. A bushing 42 may be provided to help attach with the leaf spring 14 to the lower end portions 35 of ear tubes 12. Although a stethoscope having a single leaf spring is illustrated, it is also contemplated that a double leaf spring arrangement similar to that illustrated in U.S. Pat. No. 3,168,161 or 3,504,760, which are hereby incorporated by reference, may be used. Additional construction details and methods may be found in coassigned U.S. Pat. No. 4,200,169 to MacDonald et al., which is also incorporated herein by reference. Additional discussion about the dip-molding process, particularly methods and compositions suitable for stethoscopes, can be found in U.S. Pat. No. 5,324,471, "Method of forming a molded article using a mold having an elastomeric mold member" to Packard et al., with is hereby incorporated by reference in its entirety. Although polyvinyl chloride is now considered preferred, other polymers that can be prepared in a dual-lumen configuration are considered to be within the scope of the invention.

Referring to this figure, it will be understood that any particular binaural 11 must be fabricated to a predetermined length. Molded-in connection 25 is adapted to receive the stem 24, and this cannot be modified after fabrication. If one were to cut flexible tubing 20 to a shorter length, wall 23 would prevent the stem 24 from engaging the flexible tubing 20.

Figure 2:
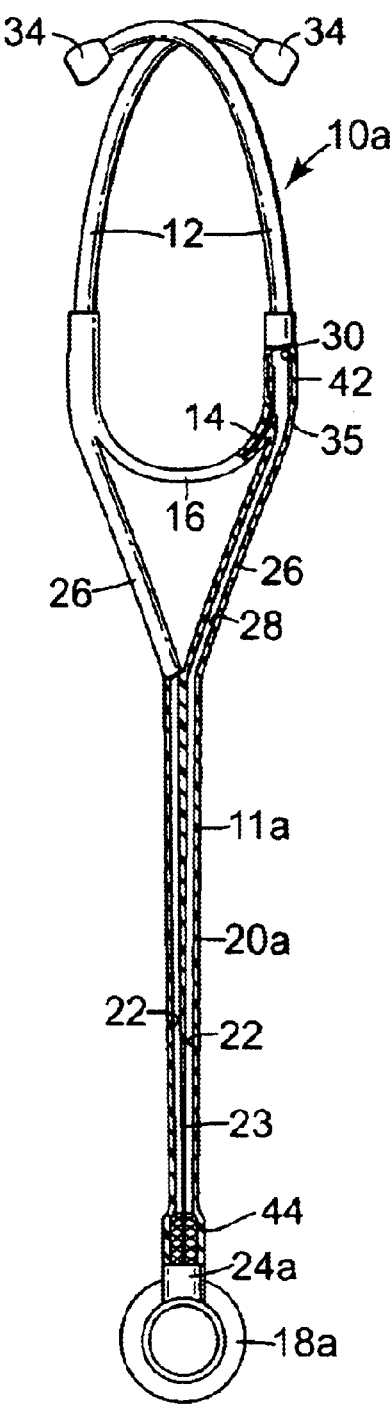
FIG. 2 is a face view of a stethoscope according to the present invention, broken away and shown in section.

Referring out to FIG. 2, an exemplary stethoscope according to the present invention is illustrated in a view similar to that of FIG. 1. There is of the 10a according to the present invention, the binaural 11a does not have a molded-in connection 25; the wall 23 extends as far as the end of the flexible tubing 20a and is received in a slot 44 in stem 24a. This arrangement offers the advantage that the flexible tubing 20a can be manufactured in one length in each color, specifically in the longest length that consumers prefer. When a customer orders a shorter length, that one manufactured size can be cut down with a knife to the preferred length and stem 24a provided by the present invention will receive it securely. As a further advantage, if the consumer receives the stethoscope and later decides that a shorter length is more suited to their needs, the flexible tubing 20a may be shortened with household tools.

The chestpiece 18a may be any appropriate chestpiece having good acoustical quality. The chestpiece 18a may be a conventional type, having e.g. one diaphragm-type microphone and one bell-type microphone. The diaphragm is regarded as better for picking up higher frequency sounds and the bell is preferred for the lower frequencies. The bell is in essence an open cup which is placed over the desired spot on the body and the diaphragm is similar but with a membrane or diaphragm stretched over the mouth of the cup. The detailed design of chestpieces has been the subject of much variation, for the purpose of maximizing the useful audio information that can be collected. Various shapes and configurations are known. Combination chestpieces which can be used in either mode are common (U.S. Pat. No. 3,951,230) and are preferred in the present invention.

Alternatively, the microphone on chestpiece 18a may be at the so-called tunable type, which has a diaphragm supported by a flexible surround. With a tunable microphone, the diaphragm may be held lightly against the patient's body in order to emphasize lower frequency sounds. If the diaphragm is pressed sufficiently firmly against the patient's body, it will contact an annular ring mounted behind the diaphragm which will cause the acoustical characteristics of microphone to change, specifically to attenuate lower sound frequencies. Additional discussion of this phenomenon can be found in coassigned U.S. Pat. No. 4,440,258 to Packard, the entire contents of which are hereby incorporated by reference.

Figure 3:
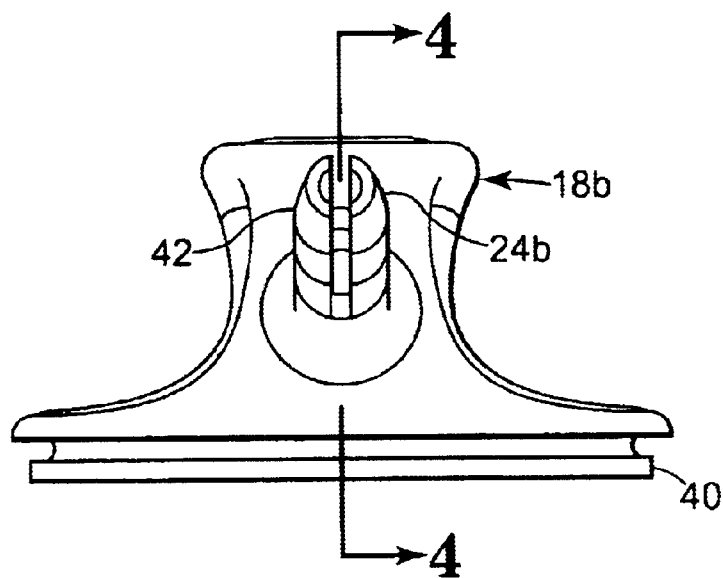
FIG. 3 is an endview of the chestpiece of the stethescope illustrated in isolation according to one embodiment of the invention.

A chestpiece adapted for use with a tunable microphone is illustrated in FIG. 3. This chestpiece 18b includes a stem 24b according to the present invention. The chestpiece 18b includes an annular flange 40 to support a flexible surround as will be described with more particularity in connection with FIG. 4. In this figure, it can be seen that the stem 24b may have barbs 42 to assist in retaining binaural 11a. In alternate embodiments, other expedients such as e.g., knurling, adhesives, an external ferrule or simple friction assist in retaining binaural 11a.

Figure 4:
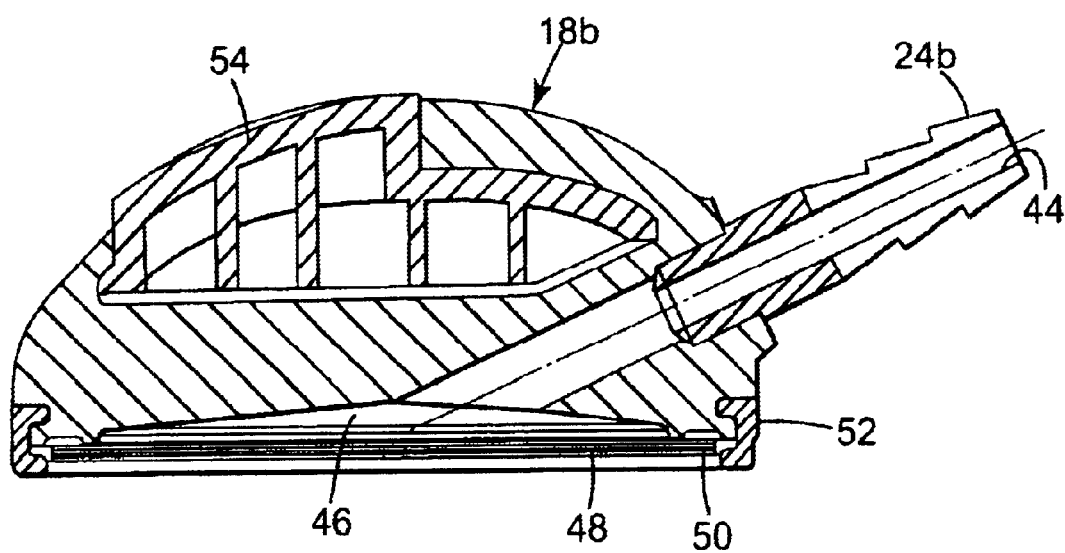
FIG. 4 is a cross sectional view of the chestpiece of FIG. 3 taken along section lines 4—4.

Referring now to FIG. 4, the chestpiece 18b from FIG. 3, is seen in cross section. In this view, a bore 44 for the transmission of sound through stem 24b can be seen. The tunable microphone 46 includes a diaphragm 48 supported by a flexible surround 50 held onto the tunable microphone 46 by a rim 52. The illustrated embodiment includes a grip 54 injection molded from polymeric material to provide ease of handling.

Figure 5:
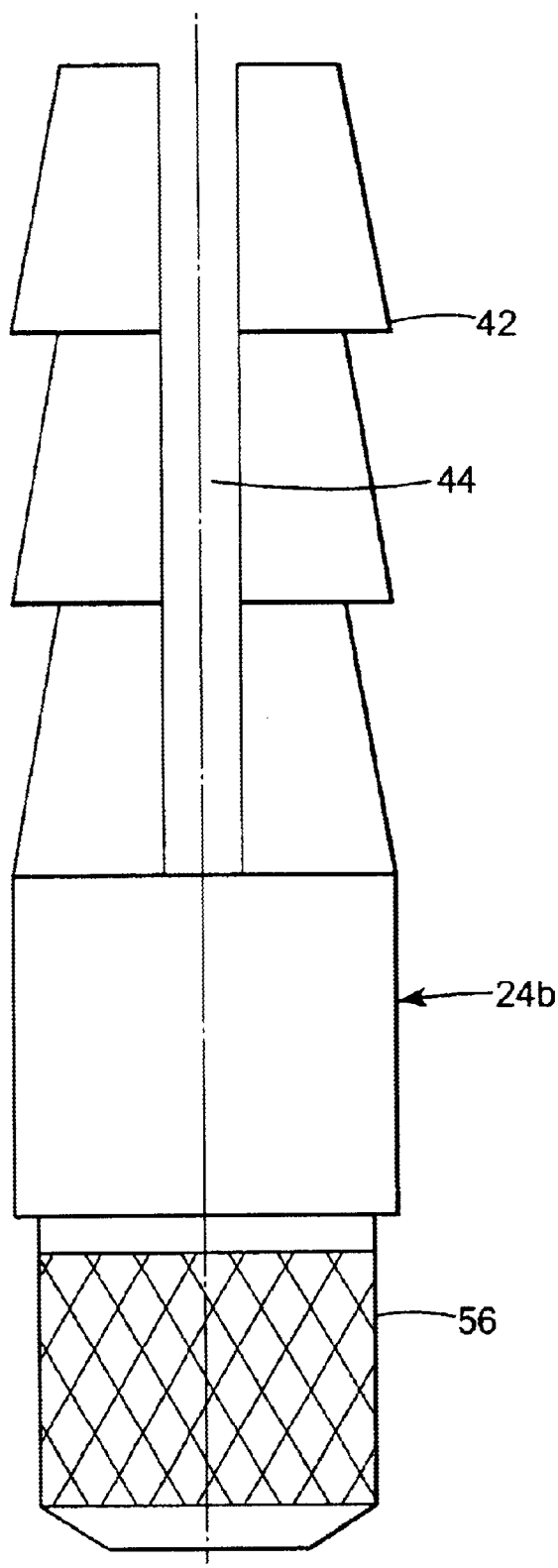
FIG. 5 is a plan view of the stem according to one embodiment of the invention.

Referring now to FIG. 5, stem 24b is seen in isolation. In this view, it will be noted that a knurled region 56 may be provided to assist in retaining the stem 24b within the remainder of the chestpiece 18b.

A number of different ear tips are considered usable with the present invention. Relatively hard, but low-friction, polymeric ear tips fabricated from e.g. Delrin™ are preferred by some users. Softer ear tips which conform to the outer ear of the wearer are also popular. The conformable ear tips disclosed in coassigned U.S. Pat. No. 4,913,259, which is hereby incorporated by reference, are considered preferred. Custom indicia may be added to e.g. the chestpiece 18b by such methods as stamping, laser marking, and chemical etching after masking.

Various modifications and alterations of the present invention will be apparent to those skilled in the art without departing from the scope and spirit of this invention, and it should be understood that this invention is not limited to the illustrative embodiments set forth herein. The claims follow.

What is claimed is:

1. A stethoscope comprising:
    at least one pair of elongated ear tubes each having an upper end for insertion into the ear of a wearer, a lower end for attaching to tubing and at least one sound passageway extending lengthwise therethrough having an interior diameter;
    at least one chestpiece having an adapter comprising a hollow stem having a slot therein; and
        tubing acoustically connecting the at least one chestpiece to the ear tubes;
        wherein the tubing comprises a wall that defines separate twin passages extending throughout the length of the tubing, the wall extending into the slot of the hollow stem of the chestpiece thereby forming twin air columns extending between the at least one chestpiece and the upper ends of the ear tubes.

2. The stethoscope according to claim 1 wherein each of the passages is connected to one of the ear tube passageways by a junction that is substantially sealed to air.

3. The stethoscope according to claim 1 wherein the twin passages are side-by-side in a common structure for a major portion of their length.

4. The stethoscope according to claim 1 wherein the twin passages diverge along their length from the chestpiece to the ear tubes.

5. The stethoscope according to claim 1 wherein the tubing is attached to a single chestpiece.

6. The stethoscope according to claim 1 wherein the interior diameter of the ear tubes has a circular cross-section throughout its length.

7. The stethoscope according to claim 1 further comprising flexible earpieces attached to the upper end of the ear tubes to provide a cushion between the ear tubes and the ears of the wearer.

8. A stethoscope comprising:
    a binaural having an upper end for insertion into the ear of a wearer, a lower end for attaching to tubing and a microphone in acoustic communication having at least one sound passageway extending lengthwise therethrough having a diameter;
    at least one microphone in acoustic communication through an adapter comprising a hollow stem having a slot therein; and
        tubing acoustically connecting the at least one microphone to the binaural;
        wherein the tubing comprises a wall that define separate twin lumens extending throughout the length of the tubing, the wall extending into the slot of the hollow stem of the microphone thereby forming twin air columns extending between the at least one microphone and the upper ends of the binaural.

9. The stethoscope according to claim 8 wherein each of the lumens is connected to the binaural by a junction that is substantially sealed to air.

10. The stethoscope according to claim 8 wherein the lumens are side-by-side in a common structure for a major portion of their length.

11. The stethoscope according to claim 8 wherein the lumens diverge along their length from the microphone to the binaurals.

12. The stethoscope according to claim 8 wherein the tubing is attached to a single microphone.

13. The stethoscope according to claim 8 wherein the interior diameter through the binaural has a circular cross-section throughout its length.

14. The stethoscope according to claim 8 further comprising flexible earpieces attached to the upper end of the binaural to provide a cushion between the binaural and the ears of the wearer.

15. A method of making a stethoscope, comprising the steps of:
    fabricating a chestpiece comprising at least one microphone in acoustic communication with a hollow stem, the stem having a slot therein;
    fabricating an binaural having twin passages separated by a wall;
    cuffing the binaural to a desired length as determined by a customer; and
    assembling the stethoscope by engaging the binaural with the stem, and disposing the wall within the slot.

16. The method of claim 15 further comprising the step of customizing the stethoscope according to at least one additional custom feature determined by the customer.

17. The method according to claim 15 wherein at least one additional feature is selected from the group consisting of tubing assembly color, microphone type, and eartip type.

18. A method of making a stethoscope, comprising the steps of:
    fabricating a chestpiece comprising at least one microphone with a hollow stem, the stem having a slot therein;
    fabricating a binaural having twin lumens separated by a wall;
    cutting the binaural to a desired length as determined by a customer; and
    assembling the stethoscope by engaging the binaural with the stem, and disposing the wall within the slot; and
    customizing the stethoscope according to a feature determined by a customer.

19. The method of claim 18 further comprising the step of customizing the stethoscope according to at least one additional custom feature determined by the customer.

20. The method according to claim 18 for wherein at least one additional feature is selected from the group consisting of tubing assembly color, microphone type, and eartip type.

* * * * *

UNITED STATES PATENT AND TRADEMARK OFFICE
CERTIFICATE OF CORRECTION

| | |
|---|---|
| PATENT NO. | : 6,691,821 B2 |
| APPLICATION NO. | : 09/948971 |
| DATED | : February 17, 2004 |
| INVENTOR(S) | : Craig D. Oster |

It is certified that error appears in the above-identified patent and that said Letters Patent is hereby corrected as shown below:

Title Page
Item (54) Title Line, replace "SPILT" with -- SPLIT -- ;

Title Page
Item (56) References Cited, Under U.S. Patent Documents, "Littman" and Littman" should be -- Littman -- ;

Column 1
Line 1, replace the word "SPILT" with -- SPLIT -- ;

Column 1
Line 36, replace the word "Stethescopes" with -- Stethoscopes -- ;

Column 3
Line 5, replace the word "stethescope" with -- stethoscope -- ;

Column 3
Line 50, replace the word "No." with -- Nos. -- ;

Column 3
Line 59, replace the word "with" with -- which -- ;

Column 4
Line 4, after the word "stethoscope" insert -- 10a -- ;

Column 4
Line 6-7, delete "There is of the 10a according to the present invention, the" ;

Column 6
Line 33, replace the word " cuffing" with -- cutting -- ;

UNITED STATES PATENT AND TRADEMARK OFFICE
CERTIFICATE OF CORRECTION

PATENT NO. : 6,691,821 B2
APPLICATION NO. : 09/948971
DATED : February 17, 2004
INVENTOR(S) : Craig D. Oster It is certified that error appears in the above-identified patent and that said Letters Patent is hereby corrected as shown below:

Column 6
Line 51, replace the word "binaural" with -- binaural -- .

Signed and Sealed this

Tenth Day of July, 2007

JON W. DUDAS
*Director of the United States Patent and Trademark Office*